United States Patent [19]

Bertolini et al.

[11] Patent Number: 5,081,136
[45] Date of Patent: Jan. 14, 1992

[54] 1,2,3-TRIAZOLE COMPOUNDS ACTIVE AS INHIBITORS OF THE ENZYME HMG-COA REDUCTASE AND PHARMACEUTICAL COMPOSITIONS CONTAINING THEM

[75] Inventors: Girogio Bertolini, Milan; Cesare Casagrande, Arese; Francesco Santangelo, Milan, all of Italy

[73] Assignee: Zambon Group S.p.A., Vicenza, Italy

[21] Appl. No.: 626,762

[22] Filed: Dec. 13, 1990

[30] Foreign Application Priority Data

Dec. 21, 1989 [IT] Italy ................... 22768 A/89

[51] Int. Cl.$^5$ ................... A61K 31/41; A61K 31/44; C07D 249/06; C07D 401/14
[52] U.S. Cl. ................... 514/359; 514/333; 514/340; 546/256; 546/276; 548/255
[58] Field of Search ............... 546/256, 276; 548/255; 514/333, 340, 359

[56] References Cited

U.S. PATENT DOCUMENTS 4,808,607 2/1989 Wareing et al. ................... 548/343

Primary Examiner—Patricia L. Morris
Attorney, Agent, or Firm—Stevens, Davis, Miller & Mosher

[57] ABSTRACT

Compounds of formula

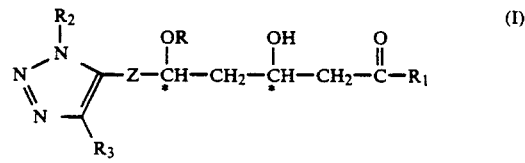

wherein R, $R_1$, $R_2$, $R_3$ and Z have the meanings reported in the specification, and intermediates for their preparation are described. The compounds of formula I have antiatherosclerotic activity as inhibitors of the enzyme HMG-CoA reductase and they are useful in the pharmaceutical field. Compositions for pharmaceutical use containing a compound of formula I as active ingredient are described too.

7 Claims, No Drawings

1,2,3-TRIAZOLE COMPOUNDS ACTIVE AS INHIBITORS OF THE ENZYME HMG-COA REDUCTASE AND PHARMACEUTICAL COMPOSITIONS CONTAINING THEM

The present invention relates to compounds with pharmacological activity and, more particularly, it relates to compounds having anti-atherosclerotic activity as inhibitors of 3-hydroxy-3-methylglutaryl-CoA reductase (HMG-CoA reductase), the rate controlling enzyme in cholesterol biosynthesis.

Compounds having a complex structure in which a mevalolactone moiety is contained are known to control and inhibit the activity of HMG-CoA reductase. Among these, for example, Lovastatin (Merck Index, XI ed., No. 5460, page 878), isolated as fungal metabolite from *Monascus ruber* and from *Aspergillus terreus*, and Mevastatin (Merck Index, XI ed., No. 6088, page 969), isolated as fungal metabolite from *Penicillum citrinum*, may be cited.

Several derivatives of mevalolactone have been studied and, in particular, many arylalkyl derivatives of mevalolactone (wherein the aryl may be also a heterocycle) showed to be useful for treating hyperlipidaemia.

Among the disclosed compounds those in which the aryl is an 1-substituted polyhydronaphthalene (European patent application No. 283,123—Merck & Co. Inc.), a 2-substituted imidazole (International patent application No. 86/07054—Sandoz A. G.), a 2-substituted indole (International patent application No. 84/02131—Sandoz A. G.) or an 1-substituted pyrrole (European patent application No. 179,559—Warner-Lambert Co.) may be cited.

We have now found, and they are an object of the present invention, compounds of formula

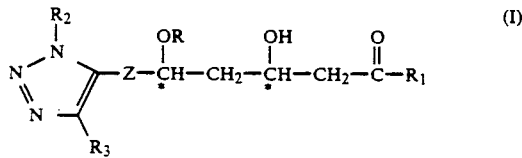

wherein
R is a hydrogen atom;
$R_1$ is a hydroxyl or an $-OR_4$ group wherein $R_4$ is a $C_1$-$C_4$ alkyl or a benzyl; or R and $R_1$, together, are a single bond between the oxygen atom and the carbonyl group;
$R_2$ is a hydrogen atom, a $C_1$-$C_5$ alkyl group, a $C_3$-$C_7$ cycloalkyl or cycloalkylmethyl group, phenyl or benzyl optionally substituted by 1 or 2 substituents selected among halogen atoms and $C_1$-$C_4$ alkyl, a pyridyl or N-oxide thereof;
$R_3$ has the meanings of $R_2$ or, in addition, is a $C_1$-$C_5$ alkoxy group, a halogen atom, a $CF_3$ or CN group;
Z is a $-(CH_2)_m-$ group wherein m is 2 or 3, a $-CH_2-CH=CH-$, $-CH=CH-CH_2-$ or $-CH=CH-$ group;
the carbon atoms marked by an asterisk are in R or S configuration and in syn relative configuration; and, when $R_1$ is a hydroxyl group, their pharmaceutically acceptable salts.

Specific examples of alkyl, alkoxy and cycloalkyl are methyl, ethyl, propyl, isopropyl, n.butyl, isobutyl, tert.butyl, n.pentyl, isopentyl, methoxy, ethoxy, propoxy, butoxy, isopropoxy, isobutoxy, tert-butoxy, cyclopropyl, cyclobutyl, cyclopentyl and cyclohexyl.

Examples of suitable pharmaceutically acceptable salts are the salts with an alkali metal, for example sodium or potassium, and with an alkaline earth metal, for example calcium or magnesium, the sodium salt being preferred.

Preferred compounds of formula I are the compounds where $R_2$ is a hydrogen atom, a $C_1$-$C_4$ alkyl group, a $C_3$-$C_5$ cycloalkyl or cycloalkylmethyl group, phenyl or benzyl optionally substituted by 1 or 2 substituents selected among fluorine, chlorine, bromine atoms and methyl groups; $R_3$ is a hydrogen atom, a $C_1$-$C_4$ alkyl or alkoxy group, a $C_3$-$C_5$ cycloalkyl or cycloalkylmethyl group, phenyl or benzyl optionally substituted by 1 or 2 substituents selected among fluorine, chlorine, bromine atoms and methyl groups.

More preferred compounds of formula I are the compounds wherein $R_2$ is methyl, ethyl, propyl, isopropyl, tert.butyl, phenyl, 4-fluorophenyl, 4-chlorophenyl, 4-bromophenyl or 4-methylphenyl; $R_3$ is methyl, ethyl, propyl, isopropyl, tert.butyl, methoxy, ethoxy, propoxy, isopropoxy, phenyl, 4-fluorophenyl, 4-chlorophenyl, 4-bromophenyl or 4-methylphenyl; Z is a $-(CH_2)_m-$ group wherein m is 2 or a $-CH=CH-$ group.

Specific examples of preferred compounds according to the present invention are:

6-[2-[1-(4-fluorophenyl)-4-isopropyl-1,2,3-triazol-5-yl]-ethyl]-4-hydroxy-tetrahydropyran-2-one 7-[1-(4-fluorophenyl)-4-isopropyl-1,2,3-triazol-5-yl]-3,5-dihydroxy-heptanoic acid 6-[2-[1-(4-fluorophenyl)-4-isopropyl-1,2,3-triazol-5-yl]-ethenyl]-4-hydroxy-tetrahydropyran-2-one 7-[1-(4-fluorophenyl)-4-isopropyl-1,2,3-triazol-5-yl]-3,5-dihydroxy-6-heptenoic acid 6-[2-[1-(4-methylphenyl)-4-isopropyl-1,2,3-triazol-5-yl]-ethyl]-4-hydroxy-tetrahydropyran-2-one 7-[1-(4-methylphenyl)-4-isopropyl-1,2,3-triazol-5-yl]-3,5-dihydroxy-heptanoic acid 6-[2-[1-(4-methylphenyl)-4-isopropyl-1,2,3-triazol-5-yl]-ethenyl]-4-hydroxy-tetrahydropyran-2-one 7-[1-(4-methylphenyl-4-isopropyl-1,2,3-triazol-5-yl]-3,5-dihydroxy-6-heptenoic acid 6-[2-(1-methyl-4-phenyl-1,2,3-triazol-5-yl)-ethyl]-4-hydroxy-tetrahydropyran-2-one 7-(1-methyl-4-phenyl-1,2,3-triazol-5-yl)-3,5-dihydroxy-heptanoic acid 6-[2-(1-methyl-4-phenyl-1,2,3-triazol-5-yl)-ethenyl]-4-hydroxy-tetrahydropyran-2-one 7-(1-methyl-4-phenyl-1,2,3-triazol-5-yl)-3,5-dihydroxy-6-heptenoic acid 6-[2-[4-(4-chlorophenyl)-1-isopropyl-1,2,3-triazol-5-yl]-ethyl]-4-hydroxy-tetrahydropyran-2-one 7-[4-(4-chlorophenyl)-1-isopropyl-1,2,3-triazol-5-yl]-3,5-dihydroxy-heptanoic acid 6-[2-[4-(4-chlorophenyl)-1-isopropyl-1,2,3-triazol-5-yl]-ethenyl]-4-hydroxy-tetrahydropyran-2-one 7-[4-(4-chlorophenyl)-1-isopropyl-1,2,3-triazol-5-yl]-3,5-dihydroxy-6-heptenoic acid 6-[2-(1-phenyl-4-methyl-1,2,3-triazol-5-yl)-ethyl]-4-hydroxy-tetrahydropyran-2-one 7-(1-phenyl-4-methyl-1,2,3-triazol-5-yl)-3,5-dihydroxy-heptanoic acid 6-[2-(1-phenyl-4-methyl-1,2,3-triazol-5-yl)-ethenyl]-4-hydroxy-tetrahydropyran-2-one 7-(1-phenyl-4-methyl-1,2,3-triazol-5-yl)-3,5-dihydroxy-6-heptenoic acid 6-[2-[4-(4-fluorophenyl)-1-isopropyl-1,2,3-triazol-5-yl]-ethyl]-4-hydroxy-tetrahydropyran-2-one
7-[4-(4-fluorophenyl)-1-isopropyl-1,2,3-triazol-5-yl]-3,5-dihydroxy-heptanoic acid
6-[2-[4-(4-fluorophenyl)-1-isopropyl-1,2,3-triazol-5-yl]-ethenyl]-4-hydroxy-tetrahydropyran-2-one
7-[4-(4-fluorophenyl)-1-isopropyl-1,2,3-triazol-5-yl]-3,5-dihydroxy-6-heptenoic acid
6-[2-[1-(4-fluorophenyl)-4-methyl-1,2,3-triazol-5-yl]-ethyl]-4-hydroxy-tetrahydropyran-2-one
7-[1-(4-fluorophenyl)-4-methyl-1,2,3-triazol-5-yl]-3,5-dihydroxy-heptanoic acid
6-[2-[1-(4-fluorophenyl)-4-methyl-1,2,3-triazol-5-yl]-ethenyl]-4-hydroxy-tetrahydropyran-2-one
7-[1-(4-fluorophenyl)-4-methyl-1,2,3-triazol-5-yl]-3,5-dihydroxy-6-heptenoic acid
6-[2-[1-(4-fluorophenyl)-4-tert.butyl-1,2,3-triazol-5-yl]-ethyl]-4-hydroxy-tetrahydropyran-2-one
7-[1-(4-fluorophenyl)-4-tert.butyl-1,2,3-triazol-5-yl]-3,5-dihydroxy-heptanoic acid
6-[2-[1-(4-fluorophenyl)-4-tert.butyl-1,2,3-triazol-5-yl]-ethenyl]-4-hydroxy-tetrahydropyran-2-one
7-[1-(4-fluorophenyl)-4-tert.butyl-1,2,3-triazol-5-yl]-3,5-dihydroxy-6-heptenoic acid
6-[2-[4-(4-fluorophenyl)-1-methyl-1,2,3-triazol-5-yl]-ethyl]-4-hydroxy-tetrahydropyran-2-one
7-[4-(4-fluorophenyl)-1-methyl-1,2,3-triazol-5-yl]-3,5-dihydroxy-heptanoic acid
6-[2-[4-(4-fluorophenyl)-1-methyl-1,2,3-triazol-5-yl]-ethenyl]-4-hydroxy-tetrahydropyran-2-one
7-[4-(4-fluorophenyl)-1-methyl-1,2,3-triazol-5-yl]-3,5-dihydroxy-6-heptenoic acid
6-[2-[1-isopropyl-4-phenyl-1,2,3-triazol-5-yl]-ethyl]-4-hydroxy-tetrahydropyran-2-one
7-[1-isopropyl-4-phenyl-1,2,3-triazol-5-yl)-3,5-dihydroxy-heptanoic acid
6-[2-[1-isopropyl-4-phenyl-1,2,3-triazol-5-yl]-ethenyl]-4-hydroxy-tetrahydropyran-2-one
7-[1-isopropyl-4-phenyl-1,2,3-triazol-5-yl]-3,5-dihydroxy-6-heptenoic acid
6-[2-[1-(4-chlorophenyl)-4-isopropyl-1,2,3-triazol-5-yl]-ethyl]-4-hydroxy-tetrahydropyran-2-one
7-[1-(4-chlorophenyl)-4-isopropyl-1,2,3-triazol-5-yl)-3,5-dihydroxy-heptanoic acid
6-[2-[1-(4-chlorophenyl)-4-isopropyl-1,2,3-triazol-5-yl]-ethenyl]-4-hydroxy-tetrahydropyran-2-one
7-[1-(4-chlorophenyl)-4-isopropyl-1,2,3-triazol-5-yl]-3,5-dihydroxy-6-heptenoic acid and the corresponding pharmaceutically acceptable salts, especially sodium salts.

The compounds of formula I inhibit the activity of HMG-CoA reductase and, therefore, they are useful as drugs in the antihypercholesterolemic therapy, in the treatment of atherosclerosis and of hyperlipidaemia.

The compounds of formula I exist in two forms, an open one when R=H (I-A) and a close one (I-B) which are easily interconvertible:

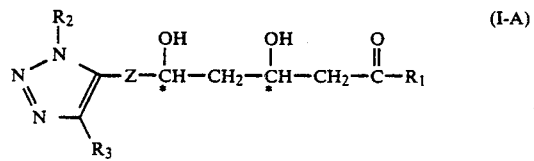

($R_1$ = OH, $OR_4$)

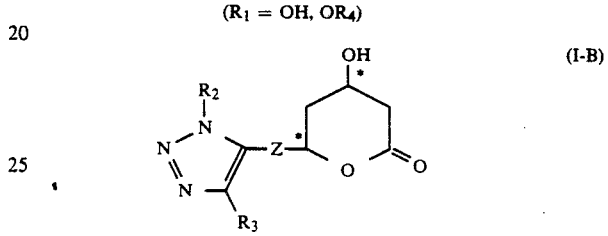

This conversion may be a chemical as well as a biological conversion. Chemically, a compound of formula I-B can be transformed into a salt of the corresponding compound of formula I-A ($R_1$=OH), for example by basic hydrolysis in mild conditions; the transformation of a compound of formula I-A into the corresponding compound of formula I-B can be carried out, instead, under acidic catalysis or by heating. Furthermore, a biological conversion of the mevalolactone ring (compound I-B) into the corresponding acid (compound I-A, R=H) usually occurs.

In this connection, it is worth noting that both compounds I-A and compounds I-B are pharmaceutically active.

The preparation of the compounds of formula I is carried out according to the reactions described in the following scheme A.

Scheme A

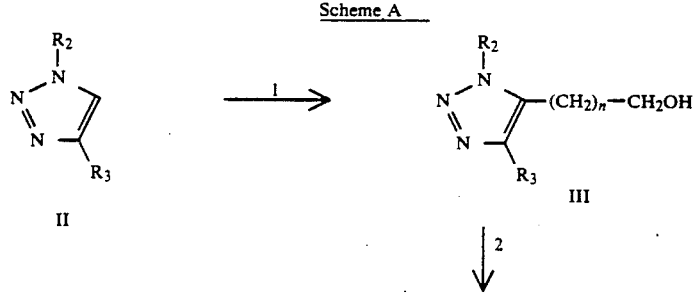

Scheme A

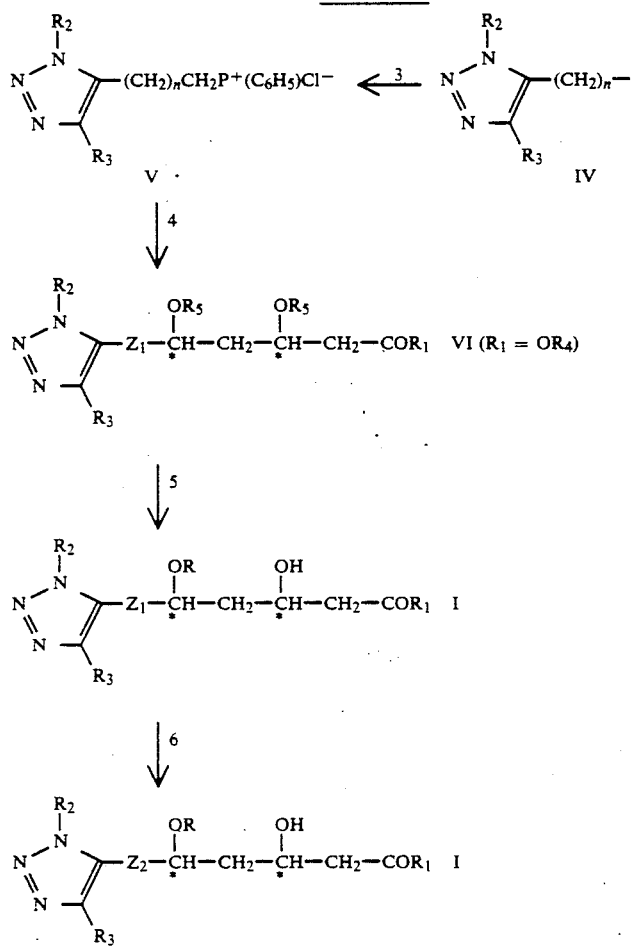

wherein

R, $R_1$, $R_2$, $R_3$ and $R_4$ have the above reported meanings;
n is 0 or 1;
$Z_1$ is a group of formula —CH=CH— or —CH=CH—CH$_2$ (n=0) or a group of formula —CH$_2$—CH=CH— (n=1);
$Z_2$ is a group of formula —(CH$_2$)$_m$— wherein m is 2 or 3;
$R_5$ is a protecting group of the hydroxy selected among trisubstituted silyl groups or the two $R_5$ together are an $R_6$—C—$R_7$ group wherein $R_6$ and $R_7$, the same or different are hydrogen atoms, $C_1$-$C_3$ alkyl groups or phenyl groups;
the carbon atoms marked by an asterisk are in R or S configuration and in syn relative configuration.

The 1,2,3-triazoles of formula II are known in the literature or they are easily prepared according to known methods. As an example, Tetrahedron Letters, 34, 3295, (1967) and Heterocyclic Chem., 1269, (1970) may be cited.

Reaction 1 consists in treating a compound of formula II with a strong base in an ethereal solvent and, then, with a suitable electrophile. In particular, suitable electrophiles are paraformaldehyde in order to prepare the compounds of formula III wherein n=0 and ethylene dioxide in order to prepare the compounds of formula III wherein n=1. Examples of ethereal solvents are tetrahydrofuran and dimethoxyethane. As a strong base, butyllithium is preferably used.

The alcohol of formula III is transformed into the corresponding chloro-derivative of formula IV by treatment with a suitable chlorinating agent in an aprotic inert solvent (reaction 2). From a practical point of view, thionyl chloride in benzene is particularly preferred.

The compound of formula IV gives the corresponding compound of formula V by treatment with triphenylphosphine at a temperature between room temperature and 100° C. in an inert solvent (reaction 3).

Reaction 4 is a typical Wittig reaction between an ylide (compound V) and an aldehyde which is known or easily preparable by known methods (International Patent Application No. 86/07054—Sandoz A. G.), such as for example (syn)-3,5-di-(diphenyl-tert.butyl-silyloxy)-5-formyl-pentanoic acid ethyl ester.

The compounds of formula VI wherein $R_1$=OR$_4$ are so obtained and, then, transformed into the corresponding compounds of formula I wherein Z=$Z_1$ and $R_1$=OR$_4$ by the deprotection of the hydroxy groups (reaction 5) followed by an optional hydrolysis of the ester in order to obtain the corresponding derivatives of formula I wherein Z=$Z_1$ and $R_1$ is different for OR$_4$.

The deprotection is carried out by known methods, for example by treatment with fluorides in acetic acid. In particular, depending on the selected conditions for carrying out the deprotection and the optional hydrolysis, the compounds of formula I wherein $R_1$=OH or the compounds of formula I-B can be obtained. The compounds of formula I wherein Z=Z₁ are useful intermediates for the preparation of the compounds of formula I wherein Z=Z₂. In fact, the compounds of formula I wherein Z=Z₁ can be reduced to the corresponding saturated compounds of formula I wherein Z=Z₂ (reaction 6).

The reduction can be carried out by catalytic hydrogenation as well as by treatment with a suitable hydride, such as triethylsilylhydride. Alternatively, the compounds of formula VI are first reduced to the corresponding compounds of formula

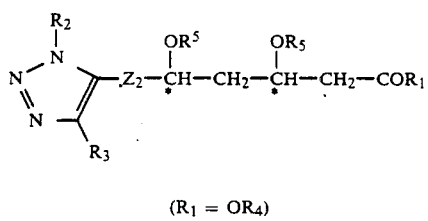

(R₁ = OR₄)

wherein R₂, R₃, R₄, R₅ and Z₂ have the above reported meanings;
the carbon atoms marked by an asterisk are in R or S configuration and in syn relative configuration; according to what above reported for reaction 6 and, then, they are deprotected, after an optional hydrolysis of the ester function, according to the already described deprotection method (reaction 5) to give the compounds of formula I wherein Z=Z₂.

An alternative process for the preparation of the compounds of formula I is reported in the following scheme B.

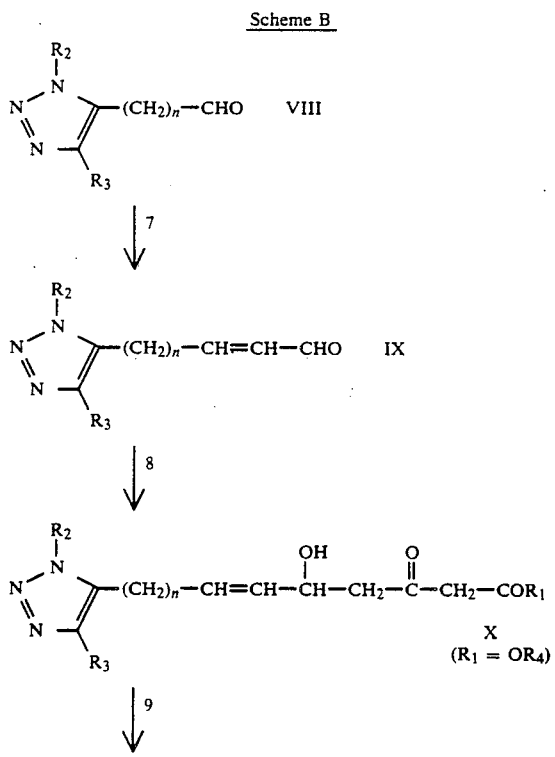

-continued
Scheme B

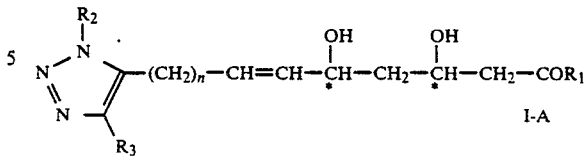

wherein R₁, R₂, R₃ and n have the above reported meanings; the carbon atoms marked by an asterisk are in R or S configuration and in syn relative configuration.

The starting compounds of formula VIII can be prepared from the corresponding alcohols of formula III (scheme A) by known oxidation reactions such as, for example, by treatment with piridinium chlorochromate in methylene chloride.

Alternatively, the aldehydes of formula VIII can be prepared by direct functionalization of the corresponding 1,2,3-triazole of formula II according to what reported for reaction 1 in scheme A. For the preparation of compounds VIII examples of suitable electrophiles are dimethylformamide (n=0) or bromoacetaldhyde and diethylacetaldehyde, followed by hydrolysis of the acetal group (n=1).

When the compounds of formula VIII are not prepared by oxidation but are prepared by direct functionalization, they can be useful for the preparation of the corresponding alcohols of formula III by reduction, for example, with a metal hydride in alcohol, such as sodium borohydride in methanol.

The selection of one among the alternative routes for the preparation of compounds II and VIII is within the normal skill of the man of the art.

From the compounds of formula VIII the α,β-unsaturated aldehydes of formula IX are prepared by known methods for the homologization of aldehydes (reaction 7).

In particular, the method described by R. H. Wollenberg et al. in J. Am. Chem. Soc., 99, 7365, (1977), may be cited. The compounds of formula IX are reacted with the dianion of an acetoacetic ester (reaction 8) according to the procedure described in Can. J. Chem., 52, 2157, (1974), in order to obtain the compounds of formula X.

The subsequent reaction 9 is a diastereoselective reduction of compound X carried out by using a borohydride, preferably sodium or zinc borohydride, optionally in the presence of a trialkylborane, such as triethylborane, or of an alkoxy-dialkylborane, such as methoxydiethylborane, in an inert solvent under inert atmosphere and at a temperature between −80° C. and 30° C. Examples of suitable inert solvent are ethers, such as dimethoxyethane, alcohols, such as methanol and ethanol, or mixtures thereof. The compounds of formula I-A wherein R₁=OR₄ and Z is —CH=CH— (n=0) or —CH₂—CH=CH— (n=1) are obtained.

From these unsaturated compounds of formula I the corresponding saturated compounds I wherein Z=Z₂ can be obtained by reduction according to what reported in scheme A (reaction 6). Clearly, the compounds of formula I-A wherein R₁=OR₄ can be hydrolized to give the corresponding compounds of formula I-A wherein R₁=OH.

The latters can, optionally, be salified according to known methods by treatment with a suitable base.

Furthermore, the compounds of formula I-A ($R_1$=OH, $OR_4$), obtained by the reaction sequences reported in schemes A and B, can be converted into the corresponding compounds of formula I-B. As already reported, the conversion can be carried out by heating a compound of formula I-A wherein $R_1$=OH in an inert solvent such as toluene; alternatively, the compounds of formula I-B can be prepared from the compounds of formula I-A as well as from the compounds of formula VI or VII by treatment with aqueous hydrofluoric acid in the presence of a water-soluble organic solvent, such as for example acetonitrile, at a temperature between 0° C. and 70° C.

The salts of the compounds of formula I can be prepared also by treating a compound of formula I-B with a base. The compounds of formula I are inhibitors of the enzyme HMG-CoA reductase and, consequently, they can be used in the pharmaceutical field as antihypercholesterolemic and antiatherosclerotic agents.

The pharmacological activity of the compounds object of the present invention was evaluated by in vitro tests (example 12). For the practical use in therapy the compounds of formula I can be used in the form of pharmaceutical compositions which are an other object of the present invention. The suitable pharmaceutical compositions depend on the selected administration route.

Examples of compositions are solid pharmaceutical compositions for oral use such as capsules, tablets and granulates, liquid pharmaceutical compositions for parenteral use such as solutions or freeze-dried powders to be diluted at the moment of use. The compositions can contain one or more compounds of formula I as active ingredient together with suitable excipients for pharmaceutical use depending on the kind of the composition. The preparation of the compositions is carried out according to traditional techniques.

Optionally, the compositions object of the present invention can contain an association of a compound of formula I with another active ingredient. For this purpose, bile acid sequesterings, nicotinic acid derivatives and cholesterolacyltransferase (ACAT) inhibitors are particularly suitable.

The doses of the compounds of formula I to be administered change depending on several factors such as the selected composition, the symptoms and the age of the patient.

In any case, the daily dose will be between 10 and 500 mg to be administered in a single dose or in repeated doses.

In order to better illustrate the present invention, the following examples are given.

EXAMPLE 1

Preparation of 4-fluorophenylazide

A solution of sodium nitrite (17 g; 0.25 mol) in water (100 ml) was slowly added to a solution of 4-fluoroaniline (24 ml; 0.25 mol) and of hydrochloric acid 12N (50 ml) at a temperature between 0° and 5° C.

The solution was kept under stirring at this temperature for an hour and, then, a solution of sodium azide (16 g; 0.25 mol) in water (60 ml) was slowly added while keeping the temperature between 0° and 5° C.

After complete generation of $N_2$ under stirring at this temperature, the reaction mixture was extracted with methylene chloride (3×150 ml) and the combined organic phases were washed with water, dried on anhydrous sodium sulfate and evaporated.

The pure title compound was obtained as an oil.

$^1$H-NMR (60 MHz, CDCl$_3$): δ (ppm): 7.0–7.2 (4H, m).

Mass (chemical ionization, positive ions, ammonia): m/e 138 (M+1)$^+$, 109.

EXAMPLE 2

Preparation of 1-(4-fluorophenyl)-4-methyl-5-piperidino-4,5-dihydro-1,2,3-triazole 1-(1-propenyl)-piperidine (9.4 g; 75.07 mmol) and 4-fluorophenylazide (10.3 g; 75.07 mmol), prepared as described in example 1, were admixed at 0° C. and the resultant mixture was kept at room temperature for 54 hours in the absence of light. The obtained solid mass was collected with petroleum ether and filtered obtaining the title compound (6 g). The mother liquor was evaporated and the resultant crude compound was purified by chromatography on silica gel (230–400 mesh), eluent petroleum ether:ethyl acetate=9:1, obtaining further title compound (m.p. 75° 76° C.).

$^1$H-NMR (300 MHz, CDCl$_3$): δ (ppm): 1.25 (3H, d); 1.33–1.56 (6H, m); 2.38 (4H, t); 4.36–4.48 (2H, m); 7.03 (2H, t); 7.46 (2H, dd). Mass (chemical ionization, positive ions, ammonia): m/e 236 (M+1)$^+$. By working in a similar way the following compound was prepared:

1-(4-fluorophenyl)-4-isopropyl-5-piperidino-4,5-dihydro-1,2,3-triazole.

m.p. 81°–83° C.

$^1$H-NMR (300 MHz, CDCl$_3$): δ (ppm): 0.90 (3H, d); 0.98 (3H, d); 1.33–1.55 (6H, m); 1.92 (1H, m); 2.25 (4H, m); 4.24 (1H, dd); 4.44 (1H, d); 7.02 (2H, t); 7.45 (2H, dd).

Mass (chemical ionization, positive ions, ammonia): m/e 291 (M+1)$^+$.

EXAMPLE 3

Preparation of 1-(4-fluorophenyl)-4-methyl-1,2,3-triazole

A mixture of 1-(4-fluorophenyl)-4-methyl-5-piperidino-4,5-dihydro-1,2,3-triazole (11.8 g; 45.21 mmol), prepared as described in example 2, and a solution of potassium hydroxide 2N in methanol (300 ml) was heated under reflux for 6 hours. Methanol was evaporated and the resultant crude compound was collected with water and extracted with ethyl ether. The combined organic phases were washed with water, dried on anhydrous sodium sulfate and evaporated.

The title compound was crystallized from hexane (m.p. 97°–98° C.).

$^1$H-NMR (300 MHz, CDCl$_3$): δ (ppm): 2.43 (3H, s); 7.22 (2H, dd); 7.67 (1H, s); 7.68 (2H, dd).

Mass (chemical ionization, positive ions, ammonia): m/e 178 (M+1)$^+$. By working in a similar way the following compound was prepared:

1-(4-fluorophenyl)-4-isopropyl-182,3-triazole purified by chromatography on silica gel (230–400 mesh), eluent petroleum ether:ethyl acetate=85:15 (m.p. 89°–91° C.).

$^1$H-NMR (300 MHz, CDCl$_3$): δ (ppm): 1.36 (6H, d); 3.15 (1H, m); 7.18 (2H, dd); 7.65 (1H, s); 7.68 (2H, dd).

Mass (chemical ionization, positive ions, ammonia): m/e 206 (M+1)$^+$.

EXAMPLE 4

Preparation of
4-(4-fluorophenyl)-1-isopropyl-1,2,3-triazole

A mixture of isopropylazide [G. A. Olah, D. J. Donovan, J. Org. Chem., 43, 860, (1978)] (54.5 g; 640.3 mmol) and 4-fluorophenylacetylene [J. B. Lambert et al., J. Am. Chem. Soc., 107, 5443, (1985)] (39 g; 325.1 mmol) was heated at 70° C. for 41 hours. The excess of isopropylazide was distilled off an the resultant crude compound was purified by chromatography on silica gel (230–400 mesh), eluent methylene chloride:acetone=39:1, giving the title compound (m.p. 54°–55° C.).

$^1$H-NMR (300 MHz, CDCl$_3$): δ (ppm): 1.61 (6H, d); 4.86 (1H, m); 7.09 (2H, t); 7.73 (1H, s); 7.79 (2H, dd).

Mass (chemical ionization, positive ions, ammonia): m/e 206 (M+1)$^+$.

EXAMPLE 5

Preparation of
1-(4-fluorophenyl)-4-methyl-5-formyl-1,2,3-triazole

A 1.6M solution of butyllithium in hexane (3.8 ml; 6.10 mmol) was slowly added, at −30° C. under nitrogen, to a solution of 1-(4-fluorophenyl)-4-methyl-1,2,3-triazole (1 g; 5.81 mmol), prepared as described in example 3, in anhydrous tetrahydrofuran (19 ml). The solution was kept under stirring at −30° C. for 30 minutes, then, anhydrous dimethylformamide (10 ml) was added at 0° C. and the reaction mixture was kept under stirring at room temperature for 3 hours.

The reaction mixture was poured into water and extracted with ethyl ether.

The combined organic phases were washed with water, dried on anhydrous sodium sulfate and evaporated. The resultant crude compound was purified by chromatography on silica gel (230–400 mesh), eluent petroleum ether:ethylacetate=6:4, obtaining the title compound (m.p. 110° C.).

$^1$H-NMR (300 MHz, CDCl$_3$): δ (ppm): 2.68 (3H, s); 7.27 (2H, t); 7.52 (2H, dd); 9.95 (1H, s).

Mass (chemical ionization, positive ions, ammonia): m/e 206 (M+1)$^+$. By working in a similar way the following compounds were prepared:

1-(4-fluorophenyl)-4-isopropyl-5-formyl-1,2,3-triazole
m.p. 69°–71° C.

$^1$H-NMR (300 MHz, CDCl$_3$): δ (ppm): 1.46 (6H, d); 3.56 (1H, m); 7.26 (2H, dd); 7.53 (2H, dd); 9.97 (1H, s).

Mass (chemical ionization, positive ions, ammonia): m/e 234 (M+1)$^+$.

4-(4-fluorophenyl)-1-isopropyl-5-formyl-1,2,3-triazole
m.p. 113°–114° C.

$^1$H-NMR (60 MHz, CDCl$_3$): δ (ppm): 1.72 (6H, d); 5.58 (1H, m); 7.33 (2H, t); 7.85 (2H, dd); 10.22 (1H, s).

Mass (chemical ionization, positive ions, ammonia): m/e 234 (M+1)$^+$.

EXAMPLE 6

Preparation of
1-(4-fluorophenyl)-4-methyl-5-hydroxymethyl-1,2,3-triazole

Sodium borohydride (59 mg; 1.56 mmol) was added at 0° C. to a solution of 1-(4-fluorophenyl)-4-methyl-5-formyl-1,2,3-triazole (640 mg; 3.12 mmol), prepared as described in example 5, in methanol (15 ml) and the reaction mixture was kept under stirring at this temperature for 30 minutes.

Methanol was evaporated and the resultant crude compound was collected with a saturated ammonium chloride solution. The solution was extracted with methylene chloride and the combined organic phases were washed with a saturated sodium chloride solution, dried on anhydrous sodium sulfate and evaporated. The resultant crude compound was purified by chromatography on silica gel (239–400 mesh), eluent methylene chloride:methanol=97:3, giving the title compound (m.p. 141°–142° C.).

$^1$H-NMR (300 MHz, DMSO): δ (ppm): 2.33 (3H, s); 4.66 (2H, d); 5.50 (1H, t, hydrogen-deuterium exchange with D$_2$O); 7.46 (2H, t); 7.74 (2H, dd).

Mass (chemical ionization, positive ions, ammonia): m/e 208 (M+1)$^+$. By working in a similar way the following compounds were prepared: 1-(4-fluorophenyl)-4-isopropyl-5-hydroxymethyl-1,2,3-triazole
m.p. 101°–103° C.

$^1$H-NMR (300 MHZ, CDCl$_3$): δ (ppm): 1.38 (6H, d); 3.14 (1H, m); 4.66 (2H, d); 7.21 (2H, dd); 7.66 (2H, dd).

Mass (chemical ionization, positive ions, ammonia): m/e 236 (M+1)$^+$.

4-(4-fluorophenyl)-1-isopropyl-5-hydroxymethyl-1,2,3-triazole
m.p. 114°–116° C.

$^1$H-NMR (60 MHz, CDCl$_3$): δ (ppm): 1.62 (6H, d); 4.80 (2H, s); 4.7–5.2 (1H, m); 7.16 (2H, t); 7.71 (2H, dd).

Mass (chemical ionization, positive ions, ammonia): m/e 236 (M+1)$^+$.

EXAMPLE 7

Preparation of
1-(4-fluorophenyl)-4-methyl-5-chloromethyl-1,2,3-triazole

A solution of 1-(4-fluorophenyl)-4-methyl-5-hydroxymethyl-1,2,3-triazole (871 mg; 4.20 mmol), prepared as described in example 6, and thionyl chloride (400 ml; 5.46 mmol) in benzene (14 ml) was heated under reflux for 4 hours. The reaction mixture was kept under stirring at room temperature overnight, thionyl chloride and benzene were evaporated and the resultant crude compound was collected several times with benzene. After evaporation of the solvent, the crude compound was purified by chromatography on silica gel (230–400 mesh), eluent methylene chloride:acetone=95:5, giving the title compound (m.p. 70°–71° C.).

$^1$H-NMR (300 MHz, CDCl$_3$): δ(ppm): 2.45 (3H, s); 4.53 (2H, s); 7.25 (2H, t); 7.57 (2H, dd).

Mass (chemical ionization, positive ions, isobutane): m/e 226 (M+1)$^+$.

By working in a similar way the following compounds were prepared:

1-(4-fluorophenyl)-4-isopropyl-5-chloromethyl-1,2,3-triazole oil $^1$H-NMR (300 MHz, CDCl$_3$): δ(ppm): 1.43 (6H, d); 3.13 (1H, m); 4.54 (2H, s); 7.25 (2H, t); 7.57 (2H, dd).

Mass (chemical ionization, positive ions, ammonia): m/e 254 (M+1)$^+$.

4-(4-fluorophenyl)-1-isopropyl-5-chloromethyl-1,2,3-triazole oil $^1$H-NMR (60 MHz, CDCl$_3$): δ(ppm): 1.75 (6H, d); 4.83 (2H, s); 4.5–5.1 (1H, m); 7.29 (2H, t); 7.85 (2H, t).

Mass (chemical ionization, positive ions, ammonia): m/e 254 (M+1)$^+$.

EXAMPLE 8

Preparation of
[[1-(4-fluorophenyl)-4-methyl-1,2,3-triazol-5-yl]-methyl]-triphenylphosphonium chloride A solution of 1-(4-fluorophenyl)-4-methyl-5-chloromethyl-1,2,3-triazole (754 mg; 3.34 mmol), prepared as described in example 7, and triphenylphosphine (1.1 g; 4.18 mmol) in toluene (33 ml) was heated at 80° C. for 21 hours. Then, the reaction mixture was cooled to room temperature and kept at this temperature overnight. The precipitate was filtered by washing with a little amount of toluene and with ethyl ether. The title compound was obtained as a solid.
m.p. 292°–293° C.

$^1$H-NMR (300 MHz, DMSO): δ(ppm): 1.55 (3H, d); 5.35 (2H, d); 7.18 (2H, t); 7.34 (2H, dd); 7.47 (6H, dd); 7.63 (6H, td); 7.88 (3H, t).

By working in a similar way the following compounds were prepared:

[[1-(4-fluorophenyl)-4-isopropyl-1,2,3-triazol-5-yl]-methyl]-triphenylphosphonium chloride
m.p. 288°–291° C.

$^1$H-NMR (300 MHz, DMSO): δ(ppm): 0.84 (6H, d); 2.61 (1H, m); 5.38 (2H, d); 7.14 (2H, t); 7.36 (2H, dd); 7.45 (6H, dd); 7.65 (6H, td); 7.87 (3H, t).

[[4-(4-fluorophenyl)-1-isopropyl-1,2,3-triazol-5-yl]-methyl]-triphenylphosphonium chloride
m.p. 289°–290° C. (dec.)

$^1$H-NMR (60 MHz, CDCl$_3$): δ(ppm): 1.19 (6H, d); 4.92 (1H, m); 6.43 (2H, d); 7.02 (2H, t); 7.5–8.0 (17H, m).

Mass (chemical ionization, positive ions, ammonia): m/e 480 (M)$^+$.

EXAMPLE 9

Preparation of
(syn)-3,5-di-(diphenyl-tert.butyl-silyloxy)-7-[1-(4-fluorophenyl)-4-methyl-1,2,3-triazol-5-yl]-6-heptenoic acid ethyl ester A 1.6M solution of butyllithium in hexane (1.4 ml; 2.28 mmol) was slowly added to a suspension of [[1-(4-fluorophenyl)-4-methyl-1,2,3-triazol-5-yl]-methyl]-triphenylphosphonium chloride (926 mg; 1.90 mmol), prepared as described in example 8, in tetrahydrofuran (20 ml) at −30° C. under nitrogen. The suspension was kept under stirring at −30° C. for 15 minutes and, then, added to a solution of (syn)-3,5-di-(diphenyl-tert.butyl-silyloxy)-6-oxo-hexanoic acid ethyl ester (1.27 g; 1.90 mmol) in tetrahydrofuran (18 ml) at −30° C. under nitrogen. The resultant mixture was kept at 0° C. for 7 hours and, then, at room temperature overnight. The reaction mixture was poured into a saturated ammonium chloride solution and extracted with ethyl ether. The combined organic phases were washed with a saturated sodium chloride solution, dried on anhydrous sodium sulfate and evaporated. The resultant crude compound was purified by chromatography on silica gel (230–400 mesh), eluent petroleum ether:ethyl acetate=8:2, giving the pure title compound as an oil.

$^1$H-NMR (300 MHz, CDCl$_3$): δ(ppm): 0.90 (9H, s); 0.95 (9H, s); 1.18 (3H, t); 1.83 (2H, m); 2.12 (3H, s); 2.39 (1H, dd); 2.53 (1H, dd); 4.03 (2H, q); 4.21 (1H, m); 4.37 (1H, m); 5.56 (1H, dd); 5.57 (1H, d); 7.05–7.60 (24H, m).

By working in a similar way the following compounds were prepared:

(syn)-3,5-di-(diphenyl-tert.butyl-silyloxy)-7-[1-(4-fluorophenyl)-4-isopropyl-1,2,3-triazol-5-yl]-6-heptenoic acid ethyl ester $^1$H-NMR (300 MHz, CDCl$_3$): δ(ppm): 0.90 (9H, s); 0.94 (9H, s); 1.18 (3H, t); 1.23 (3H, d); 1.29 (3H, d); 1.83 (2H, m); 2.34 (1H, dd); 2.47 (1H, dd); 2.69 (1H, m); 4.02 (2H, q); 4.21 (1H, m); 4.37 (1H, q); 5.58 (1H, dd); 5.8 (1H, dd); 7.0–7.6 (24H, m).

(syn)-3,5-di-(diphenyl-tert.butyl-silyloxy)-7-[4-(4-fluorophenyl)-1-isopropyl-1,2,3-triazol-5-yl]-6-heptenoic acid ethyl ester $^1$H-NMR (300 MHz, CDCl$_3$): δ(ppm): 0.90 (9H, s); 1.01 (9H, s); 1.18 (3H, t); 1.38 (3H, d); 1.43 (3H, d); 1.84 (2H, m); 2.42 (1H, d); 2.54 (1H, d); 4.0–4.1 (3H, m); 4.17 (1H, m); 4.48 (1H, q); 5.48 (1H, dd); 5.97 (1H, d); 6.96 (2H, t); 7.15–7.65 (22H, m).

EXAMPLE 10

Preparation of
trans-6-[2-[1-(4-fluorophenyl)-4-methyl-1,2,3-triazol-5-yl]-ethenyl]-4-hydroxy-tetrahydropyran-2-one A solution of (syn)-3,5-(diphenyl-tert.butylsilyloxy)-7-[1-(4-fluorophenyl)-4-methyl-1,2,3-triazol-5-yl]-6-heptenoic acid ethyl ester (950 mg; 1.13 mmol), prepared as described in example 9, in a mixture of acetonitrile and hydrofluoric acid at 40% in water (20 ml) was kept under stirring at 50° C. for 10 hours. Hydrofluoric acid was neutralized with solid sodium bicarbonate and the mixture was diluted with a little amount of water and with ethyl acetate (30 ml). The salts were filtered and the solution was extracted with ethyl acetate (3×30 ml). The combined organic phases were washed with a saturated sodium chloride solution, dried on anhydrous sodium sulfate and evaporated. The resultant crude compound was purified by chromatography on silica gel (230–400 mesh), eluent methylene:acetone=7:3, giving an oil which was collected with warm ethyl ether, cooled and filtered. The title compound was obtained as a solid (m.p. 170° C.).

$^1$H-NMR (300 MHz, DMSO): δ(ppm): 1.83 (1H, ddd); 1.92 (1H, td); 2.42 (1H, dd); 2.43 (3H, s); 2.69 (1H, d); 4.14 (1H, m); 5.23 (1H, m); 5.30 (1H, d, hydrogen-deuterium exchange with D$_2$O); 6.22 (1H, dd); 6.45 (1H, d); 7.48 (2H, t); 7.60 (2H, dd).

Mass (chemical ionization, positive ions, isobutane): m/e 318 (M+1)$^+$; 300.

By working in a similar way the following compounds were prepared:

trans-6-[2-(1-(4-fluorophenyl)-4-isopropyl-1,2,3-triazol-5-yl)-ethenyl]-4-hydroxy-tetrahydropyran-2-one
m.p. 130°–132° C.

$^1$H-NMR (300 MHz, CDCl$_3$): δ(ppm): 1.42 (6H, d); 1.83 (1H, ddd); 2.07 (1H, td); 2.72 (2H, m); 3.13 (1H, m); 4.43 (1H, m); 5.31 (1H, m); 5.95 (1H, dd); 6.46 (1H, d); 7.22 (2H, t); 7.43 (2H, dd).

Mass (chemical ionization, positive ions, isobutane): m/e 346 (M+1)$^+$; 328.

trans-6-[2-(4-(4-fluorophenyl)-1-isopropyl-1,2,3-triazol-5-yl)-ethenyl]-4-hydroxy-tetrahydropyran-2-one
m.p. 169°–171° C.

$^1$H-NMR (300 MHz, CDCl$_3$): δ(ppm): 1.63 (6H, d); 1.80 (1H, ddd); 2.06 (1H, td); 2.7 (1H, dd); 2.78 (1H, dd); 4.43 (1H, m); 4.67 (1H, m); 5.36 (1H, m); 6.01 (1H, d); 6.65 (1H, d); 7.10 (2H, t); 7.62 (2H, dd).

Mass (chemical ionization, positive ions, isobutane): m/e 346 (M+1)$^+$; 328.

EXAMPLE 11

Preparation of
trans-6-[2-[4-(4-fluorophenyl)-1-isopropyl-1,2,3-triazol-5-yl]-ethyl]-4-hydroxy-tetrahydropyran-2-one Palladium at 10% on charcoal (10 mg) was added to a solution of trans-6-[2-[4-(4-fluorophenyl)-1-isopropyl-1,2,3-triazol-5-yl]-ethyl]-4-hydroxy-tetrahydropyran-2-one (104 mg; 0.301 mmol), prepared as described in example 10, in ethanol (10 ml). The suspension was hydrogenated in a Parr apparatus at room temperature and under a pressure of 2.72 atm. After 15 minutes, the catalyst was filtered and the solvent was evaporated. The resultant crude compound was purified by chromatography on silica gel (230–400 mesh), eluent methylene chloride:methanol=95:5, giving the title compound as an amorphous solid.

$^1$H-NMR (300 MHz, CDCl$_3$): δ(ppm): 1.90 (3H, d); 1.92 (3H, d); 1.96–2.2 (4H, m); 2.89 (1H, dd); 2.98 (1H, dd); 3.25 (1H, m); 3.43 (1H, m); 4.65 (1H, m); 4.85–5.0 (2H, m); 7.40 (2H, t); 7.91 (2H, dd).

Mass (chemical ionization, positive ions, isobutane): m/e 348 (M+1)$^+$; 330.

EXAMPLE 12

Evaluation of activity in vitro

1) Preparation of hepatic microsomes

Male Sprague-Dowley rats (100–125 g) were kept in a cage with a controlled light-dark cycle for 7 days, fed with a standard diet "Altromin ®" and with water ad libitum. The animals were sacrified by decapitation and the livers were immediately drawn and used for the preparation of microsomes according to the procedure described by Shapiro and Rodwell (J. Biol. Chem., 246, 3210, 1971). The resultant microsomial pellet was suspended in phosphate buffer and preserved at −80° C.

2) In vitro evaluation of HMG-CoA reductase activity

The activity of the enzyme HMG-CoA reductase was evaluated according to the method described by Goldstein and Brawn (Proc. Nat. Acad. Sci. U.S.A., 73, 2564, 1976). The incubation mixture (200 μl) consisted of: phosphate buffer 100 mM (pH 7.4), dithiothreitol 10 mM, EDTA 10 mM, NADP 25 mM, glucose-6-phosphate 20 mM, glucose-6-phosphate dehydrogenase 3 U/ml, [$^{14}$C]-HMG-CoA (New England Nuclear) 100 μM (0.08 μCi), 600 μg of microsomial proteins. Compounds of formula I or Mevastatin, as reference compound, were added to the above incubation mixture at different concentrations in order to evaluate the IC$_{50}$ values. As internal standard [$^3$H]-mevalolactone was used. Unreacted [$^{14}$C]HMG-CoA was eliminated as described by Alberts et al. (Proc. Nat. Acad. Sci. U.S.A., 77, 3957, 1980) by using columns containing AG 1-x8 resin (Bio-rad). Then, [$^{14}$C]-mevalolactone was eluted with distilled water (3×750 μl) directly into vials containing 10 ml of "Picofluor-40 ®" (Packard). The radioactivity of the samples was measured by a beta-counter series 400 (Packard). The so calculated IC$_{50}$ values showed that the compounds of formula I, object of the present invention, are about 3–4 times more active than Mevastatin in inhibiting HMG-CoA reductase activity in vitro.

What we claim is:

1. A compound of formula

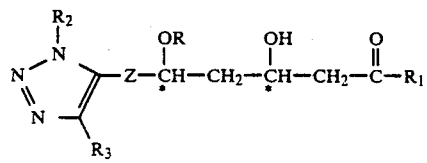

wherein

R is a hydrogen atom;

R$_1$ is a hydroxyl or an —OR$_4$ group wherein R$_4$ is a C$_1$–C$_4$ alkyl or a benzyl; or R and R$_1$, together, are a single bond between the oxygen atom and the carbonyl group;

R$_2$ is a hydrogen atom, a C$_1$–C$_5$ alkyl group, a C$_3$–C$_7$ cycloalkyl or cycloalkylmethyl group, phenyl or benzyl optionally substituted by 1 or 2 substituents selected among halogen atoms and C$_1$–C$_4$ alkyl, a pyridyl or N-oxide thereof;

R$_3$ has the meanings of R$_2$ or, in addition, is a C$_1$–C$_5$ alkoxy group, a halogen atom, a CF$_3$ or CN group;

Z is a —(CH$_2$)$_m$— group wherein m is 2 or 3, a —CH$_2$—CH=CH—, —CH=CH—CH$_2$— or —CH=CH— group;

the carbon atoms marked by an asterisk are in R or S configuration and in syn relative configuration;

and, when R$_1$ is a hydroxyl group, their pharmaceutically acceptable salts.

2. A compound according to claim 1 of formula

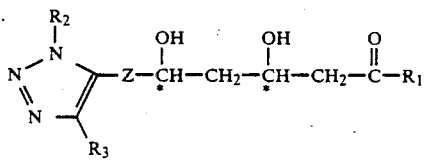

wherein

R$_1$ is a hydroxyl or an —OR$_4$ group wherein R$_4$ is a C$_1$–C$_4$ alkyl or a benzyl;

R$_2$ is a hydrogen atom, a C$_1$–C$_5$ alkyl group, a C$_3$–C$_7$ cycloalkyl or cycloalkylmethyl group, phenyl or benzyl optionally substituted by 1 or 2 substituents selected among halogen atoms and C$_1$–C$_4$ alkyl, a pyridyl or N-oxide thereof;

R$_3$ has the meanings of R$_2$ or, in addition, is a C$_1$–C$_5$ alkoxy group, a halogen atom, a CF$_3$ or CN group;

Z is a —(CH$_2$)$_m$— group wherein m is 2 or 3, a —CH$_2$—CH=CH—, —CH=CH—CH$_2$— or —CH=CH— group;

the carbon atoms marked by an asterisk are in R or S configuration and in syn relative configuration;

and, when R$_1$ is a hydroxyl group, their pharmaceutically acceptable salts.

3. A compound according to claim 1 of formula

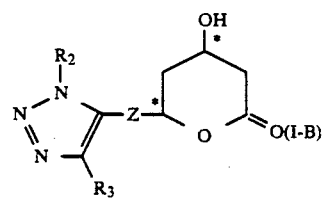

wherein $R_2$ is a hydrogen atom, a $C_1$-$C_5$ alkyl group, a $C_3$-$C_7$ cycloalkyl or cycloalkylmethyl group, phenyl or benzyl optionally substituted by 1 or 2 substituents selected among halogen atoms and $C_1$-$C_4$ alkyl, a pyridyl or N-oxide thereof;

$R_3$ has the meanings of $R_2$ or, in addition, is a $C_1$-$C_5$ alkoxy group, a halogen atom, a $CF_3$ or CN group;

Z is a —$(CH_2)_m$— group wherein m is 2 or 3, a —$CH_2$—CH=CH—, —CH=CH—$CH_2$— or —CH=CH— group;

the carbon atoms marked by an asterisk are in R or S configuration and in syn relative configuration.

4. A compound according to claims 1, 2 or 3 in which $R_2$ is a hydrogen atom, a $C_1$-$C_4$ alkyl group, a $C_3$-$C_5$ cycloalkyl or cycloalkylmethyl group, phenyl or benzyl optionally substituted by 1 or 2 substituents selected among fluorine, chlorine, bromine atoms and methyl groups; $R_3$ is a hydrogen atom, a $C_1$-$C_4$ alkyl or alkoxy group, a $C_3$-$C_5$ cycloalkyl or cycloalkylmethyl group, phenyl or benzyl optionally substituted by 1 or 2 substituents selected among fluorine, chlorine, bromine atoms and methyl groups.

5. A compound according to claims 1, 2 or 3 in which $R_2$ is methyl, ethyl, propyl, isopropyl, tert.butyl, phenyl, 4-fluorophenyl, 4-chlorophenyl, 4-bromophenyl or 4-methylphenyl; $R_3$ is methyl, ethyl, propyl, isopropyl, tert.butyl, methoxy, ethoxy, propoxy, isopropoxy, phenyl, 4-fluorophenyl, 4-chlorophenyl, 4-bromophenyl or 4-methylphenyl; Z is a —$(CH_2)_m$— group wherein m is 2 or a —CH=CH— group.

6. A pharmaceutical composition useful for the treatment of hypercholesterolemia, atherosclerosis and hyperlipidaemia and containing an effective amount of a compound according to claim 1, as active ingredient, and a carrier suitable for pharmaceutical use.

7. A method for the treatment of hypercholesterolemia, atherosclerosis and hyperlipidaemia consisting in administering a pharmaceutical effective amount of a compound according to claim 1 optionally together with a carrier suitable for pharmaceutical use.

* * * * *